(12) United States Patent  
Cho

(10) Patent No.: US 8,796,011 B2
(45) Date of Patent: Aug. 5, 2014

(54) APPARATUS FOR FABRICATING AND OPTICALLY DETECTING BIOCHIP

(75) Inventor: Seong-ho Cho, Gwacheon-si (KR)

(73) Assignee: Samsung Electronics Co., Ltd., Suwon-Si (KR)

(*) Notice: Subject to any disclaimer, the term of this patent is extended or adjusted under 35 U.S.C. 154(b) by 1087 days.

(21) Appl. No.: 12/545,315

(22) Filed: Aug. 21, 2009

(65) Prior Publication Data

US 2010/0097594 A1 Apr. 22, 2010

(30) Foreign Application Priority Data

Oct. 20, 2008 (KR) .................. 10-2008-0102559
Oct. 28, 2008 (KR) .................. 10-2008-0105924

(51) Int. Cl.
*C12M 1/34* (2006.01)
*C12M 3/00* (2006.01)
*G01N 21/64* (2006.01)
*G01N 21/25* (2006.01)
*C12M 1/00* (2006.01)

(52) U.S. Cl.
CPC .......... *G01N 21/6428* (2013.01); *G01N 21/253* (2013.01); *C12M 41/06* (2013.01)
USPC .................. 435/288.7; 435/287.2; 355/71

(58) Field of Classification Search
CPC ............ B01J 2219/00722; B01J 2219/00659; B01L 7/52; B01L 2300/0636; C40B 40/06; G01N 21/6428; G01N 21/6452; G01N 21/253; G01N 15/1475; C12M 1/3446; C12Q 1/04; G06T 7/0012; G06T 2207/30072; G06T 2207/10056; G06K 9/00
USPC ........................................... 435/287.2; 355/71
See application file for complete search history.

(56) References Cited

U.S. PATENT DOCUMENTS

| 5,190,632 A * | 3/1993 | Fujimiya et al. ............... 204/608 |
| 6,268,948 B1* | 7/2001 | Gelbart ........................ 359/231 |
| 6,271,957 B1 | 8/2001 | Quate et al. |
| 6,375,903 B1 | 4/2002 | Cerrina et al. |
| 6,480,324 B2 | 11/2002 | Quate et al. |
| 6,545,758 B1 | 4/2003 | Sandstrom |
| 6,567,163 B1 | 5/2003 | Sandstrom |
| 6,806,954 B2 | 10/2004 | Sandstrom |

(Continued)

FOREIGN PATENT DOCUMENTS

DE 199 22 942 A1 11/2000
WO WO 99/42813 A1 8/1999

(Continued)

OTHER PUBLICATIONS

European Patent Office, Partial European Search Report in European Patent Application No. 09173241.2 (Sep. 1, 2011).

*Primary Examiner* — Michael Hobbs
(74) *Attorney, Agent, or Firm* — Leydig, Voit & Mayer, Ltd.

(57) ABSTRACT

An apparatus for fabricating a biochip is provided. The apparatus includes a reaction chamber which encapsulates the biochip to be sealed form an external environment. The apparatus further includes an exposure system which has a light source and a spatial light modulator. The spatial light modulator receives light from the light source and forms an optical image utilizing the light. The optical image is received by the biochip. The apparatus further includes a detection system which detects light proceeding form the biochip.

20 Claims, 15 Drawing Sheets

(56) References Cited

U.S. PATENT DOCUMENTS

| | | |
|---|---|---|
| 7,049,049 B2 | 5/2006 | Fries |
| 7,081,954 B2 * | 7/2006 | Sandstrom .................... 356/317 |
| 7,157,229 B2 | 1/2007 | Cerrina et al. |
| 7,161,723 B1 * | 1/2007 | Silveira ........................ 359/12 |
| 7,330,255 B2 | 2/2008 | Cluzel et al. |
| 7,522,271 B2 * | 4/2009 | Sandstrom .................... 356/72 |
| 2003/0031596 A1 * | 2/2003 | Tanaami .................... 422/82.08 |
| 2003/0174324 A1 * | 9/2003 | Sandstrom .................... 356/317 |
| 2004/0144915 A1 | 7/2004 | Wagner et al. |
| 2005/0079603 A1 * | 4/2005 | Sandstrom ................. 435/288.7 |
| 2005/0249396 A1 * | 11/2005 | Cerrina et al. ................ 382/151 |
| 2006/0256332 A1 * | 11/2006 | Sandstrom .................... 356/317 |
| 2007/0154938 A1 * | 7/2007 | Oshida et al. ..................... 435/6 |
| 2008/0117489 A1 * | 5/2008 | Tanaka et al. ................. 359/224 |
| 2008/0212069 A1 * | 9/2008 | Goldberg et al. ............... 356/36 |
| 2009/0112482 A1 * | 4/2009 | Sandstrom .................... 702/19 |

FOREIGN PATENT DOCUMENTS

| | | |
|---|---|---|
| WO | WO 02/14838 A2 | 2/2002 |
| WO | WO 2004/004885 A1 | 1/2004 |
| WO | WO 2006/117556 A | 11/2006 |
| WO | WO 2008/077407 A1 | 7/2008 |

* cited by examiner

APPARATUS FOR FABRICATING AND OPTICALLY DETECTING BIOCHIP

CROSS-REFERENCE TO RELATED APPLICATIONS

This application claims priority to Korean Patent Application No. 10-2008-0102559, filed on Oct. 20, 2008, and Korean Patent Application No. 10-2008-0105924, filed on Oct. 28, 2008, and all the benefits accruing therefrom under 35 U.S.C. §119, the contents of which in its entirety are herein incorporated by reference.

BACKGROUND

1. Field

One or more exemplary embodiments relate to an apparatus for fabricating a biochip by using a photolithographic method without using a mask, and for optically detecting the biochip so as to read the biochip.

2. Description of the Related Art

A biochip is a biometric device made by combining biogenic organic materials such as enzymes, peptides, proteins, antibodies, and deoxyribonucleic acids ("DNAs") of living creatures, microorganisms, and cells, organs, and nerves of animals and plants into a microchip similar to a semiconductor chip. In particular, a DNA chip is a device for detecting DNAs. The DNA chip is made by arranging several hundred DNAs to ten million DNAs having different base sequences, of which functions in a cell are clarified, within a small space on a substrate. Furthermore, the DNAs are arranged in a single spiral shape instead of a double spiral shape on the substrate. The substrate can be a glass substrate or a semiconductor substrate for example. A collection of single spiral shaped DNAs having the same base sequence is generally referred to as a spot and nearly twenty to hundred bases are connected to form a single spot.

When genetic material of a sample is dropped onto such a DNA chip, only genes corresponding to a specific spot, i.e., genes having a complementary sequence to a base sequence of the specific spot, are combined with the corresponding spot. Furthermore, genes that are not combined with spots in the DNA chip are washed away. Functions of base sequences of spots arranged on a DNA chip are already known, and thus genetic information of the sample can be easily obtained by identifying spots combined with genes on the DNA chip. Accordingly, aspects of unique genetic expressions or mutations in a specific cell or a tissue can be analyzed relatively fast by using the DNA chip. Furthermore, the DNA chip can also be used in massive analysis of genetic expressions, single nucleotide polymorphism and copy number variation in a gene, a pathogenic bacteria infection test, an antibiotic-resistance test, research on biological reactions with respect to environmental factors, food safety inspection, identification of criminals, development of new drugs, and medical inspection of animals and plants.

Such a biochip can be fabricated by stacking DNA bases such as adenine (A), guanine (G), cytosine (C), and thymine (T) in different sequences on spots of the biochip, for example, twenty to hundred times. A very precise fabricating method is utilized to form several ten million of different spots in a single biochip with exact base sequences. A representative method of fabricating a biochip is a photolithographic method which is the same method used for fabricating a semiconductor. In the photolithographic method, a biochip except for an area for reacting with a specific base is covered by a mask and light is projected onto the biochip. In this exemplary embodiment, all bases used for reaction are combined with a photolabile material such that the bases cannot combine with each other. However, when light is projected, the photolabile material is decomposed from the bases and thus a base onto which light is projected can combine with another base. Accordingly, the specific base can be combined with bases that are not covered by the mask and are exposed to light. In the photolithographic method, although the biochip can be precisely fabricated, a fabricating time is relatively long and a fabricating cost is relatively high because the lithography equipment is relatively expensive and a large number of masks corresponding to about four times of the number of stacked bases are used.

Meanwhile, when a sample is analyzed, various methods for identifying spots in a DNA chip, which are combined with genes of the sample, have been suggested. A fluorescent light detection method is a representative example of the suggested methods. In the fluorescent light detection method, a base including a fluorescent material for emitting light of a specific color when excited by excitation light is combined with genetic material of the sample. The genetic material of the sample is dropped onto a DNA chip and then a fluorescent image obtained by projecting excitation light onto the DNA chip is analyzed, thereby indentifying spots combined with genes of the sample.

In general, a photodetector for obtaining a fluorescent image by projecting excitation light onto a DNA chip obtains a fluorescent image by detecting a DNA chip in pixels of approximately 0.1 μm to 10 μm. Such a basic detecting unit is referred as a segment, and a single spot is formed of several segments to several tens of segments (e.g., 32 segments). A segment is a basic scanning unit in a spot detection method and a panel formed of several hundred spot arrays to several thousand spot arrays (e.g., 5,000 spot arrays) is a basic scanning unit in an image detection method. Generally, the spot detection method uses a photomultiplier tube ("PMT") as the photodetector and the image detection method uses a charge-coupled device ("CCD"), a complementary metal-oxide-semiconductor ("CMOS") image sensor ("CIS"), or the like as the photodetector. A bio-chip scanner, i.e., a fluorescence detector, may read a DNA chip by scanning each segment or panel in the DNA chip.

However, since a process of fabricating a DNA chip is separated from a process of analyzing a sample, and an apparatus for fabricating the DNA chip is separated from a fluorescence detector for reading the DNA chip, exposure to an external environment is unavoidable when the DNA chip is reprocessed, stored, and used to analyze a sample, which degrades a reliability of the DNA chip.

SUMMARY

One or more exemplary embodiments include an apparatus for fabricating a biochip such as a deoxyribonucleic acid ("DNA") chip by using a photolithographic method without using a mask, and directly analyzing a sample by optically detecting the DNA chip.

One or more exemplary embodiments include an apparatus for fabricating and optically detecting a biochip, and monitoring a process of fabricating the biochip.

One exemplary embodiment may include an apparatus for fabricating a biochip, the apparatus including a reaction chamber which encapsulates the biochip to be sealed from an external environment; an exposure system which has a light source and a spatial light modulator ("SLM"), the SLM receives light from the light source and forms an optical image utilizing the received light, the optical image being received by the biochip; and a detection system which detects light proceeding from the biochip.

In one exemplary embodiment, the SLM may be a reflective SLM.

In one exemplary embodiment, the apparatus may further include an optical path changing unit which provides the light emitted from the light source to the SLM, and provides light reflected from the SLM to the reaction chamber, and provides light proceeding from the reaction chamber to the detection system.

In one exemplary embodiment, the optical path changing unit may include a polarizing beam splitter which is disposed between the light source and the SLM; a polarizer which is disposed between the light source and the polarizing beam splitter; and a quarter-wavelength ("λ/4") plate which is disposed between the polarizing beam splitter and the SLM.

In one exemplary embodiment, the exposure system may further include a light diffusion device which is disposed between the light source and the polarizer; a lens device or a mirror device which is disposed between the λ/4 plate and the SLM; a distortion correction device which is disposed between the polarizing beam splitter and the reaction chamber; and a projection optical system which is disposed between the distortion correction device and the reaction chamber.

In one exemplary embodiment, the distortion correction device may include a deformable mirror having a reflective surface which is deformable in response to at least one of mechanical and electrical manipulation for correcting distortion of an optical image.

In one exemplary embodiment, the detection system may be disposed such that the detection system faces one of light exit surfaces of the polarizing beam splitter in order to detect an optical image proceeding from the reaction chamber through the polarizing beam splitter.

In one exemplary embodiment, the optical path changing unit may further include an additional λ/4 plate which is disposed between the polarizing beam splitter and the reaction chamber.

In one exemplary embodiment, the detection system may be disposed proximate to the reaction chamber along a direction in which light proceeds, in order to detect an optical image which is transmitted through the reaction chamber and the biochip.

In one exemplary embodiment, the apparatus may further include an additional distortion correction device which is disposed between the reaction chamber and the detection system.

In one exemplary embodiment, the SLM may be a transmissive SLM.

In one exemplary embodiment, the exposure system may further include a light diffusion device and at least one of a lens device and a mirror device which are sequentially disposed between the light source and the SLM along a direction where light proceeds; and a distortion correction device and a projection optical system which are sequentially disposed between the SLM and the reaction chamber along a direction where light proceeds.

In one exemplary embodiment, the apparatus may further include an optical path changing unit which provides light emitted from the light source to the reaction chamber, and provides light proceeding from the reaction chamber to the detection system.

In one exemplary embodiment, the optical path changing unit may include a polarizing beam splitter which is disposed between the light diffusion device and at least one of the lens device and the mirror device; a polarizer which is disposed between the light diffusion device and the polarizing beam splitter; and a λ/4 plate which is disposed between the polarizing beam splitter and the at least one of the lens device and the mirror device.

In one exemplary embodiment, the light source of the exposure system may include a first light source which emits exposure light which is received by an optical multiplexer; and a second light source which emits excitation light which is received by an optical multiplexer, and the optical multiplexer selectively transmits or blocks one of the exposure light emitted from the first light source and the excitation light emitted from the second light source.

In one exemplary embodiment, the apparatus may further include an optical fiber which is disposed between the first light source and the optical multiplexer and further between the second light source and the optical multiplexer.

In one exemplary embodiment, the detection system may include an excitation light absorption filter, at least one of an imaging lens and an imaging mirror, and a photodetector which are sequentially disposed along a direction in which light proceeds.

In one exemplary embodiment, the excitation light absorption filter may be separated from an optical path when the biochip is fabricated.

In one exemplary embodiment, the photodetector may be formed of an array including a plurality of micro pixels, and may include one of a photomultiplier tube ("PMT"), a charge-coupled device ("CCD"), and a complementary metal-oxide-semiconductor ("CMOS") image sensor ("CIS").

BRIEF DESCRIPTION OF THE DRAWINGS

The above and other aspects, advantages, and features of exemplary embodiments will become more apparent by describing in further detail exemplary embodiments thereof with reference to the accompanying drawings, in which.

DETAILED DESCRIPTION

Figure 1:
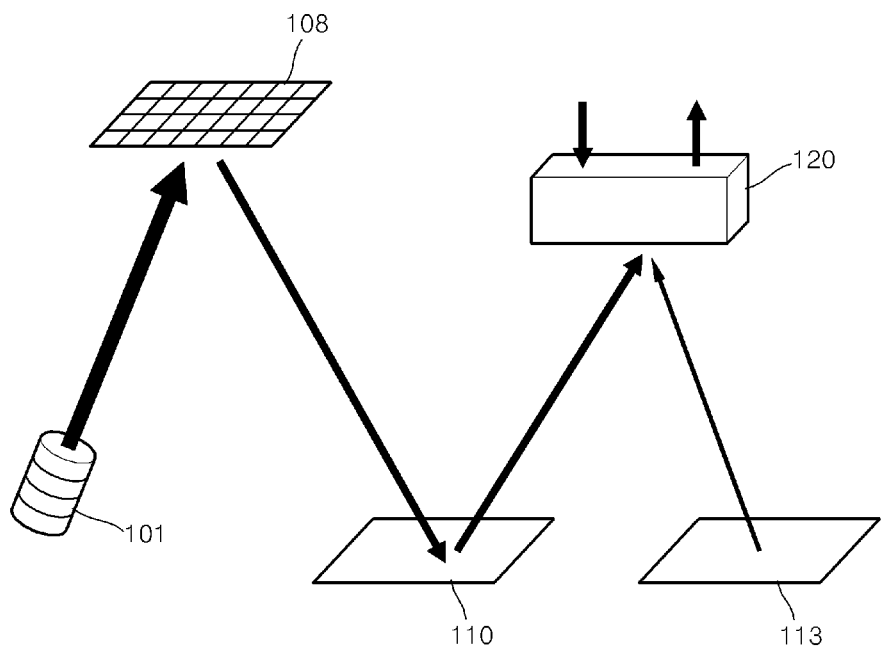
FIG. 1 is a schematic diagram of an exemplary embodiment of an apparatus for fabricating a biochip.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

Hereinafter, the present invention will be described in detail with reference to the accompanying drawings.

FIG. 1 is a schematic diagram of an exemplary embodiment of an apparatus for fabricating a biochip without using a mask.

Figure 3A:
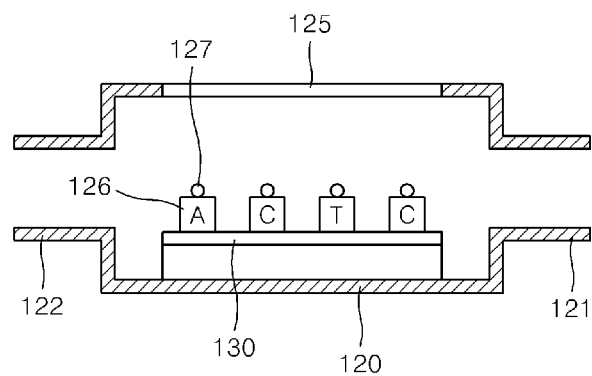
FIGS. 3A-3E are sequential diagrams of another exemplary embodiment of a process of fabricating a biochip by using the apparatus illustrated in FIG. 2.

Referring to FIGS. 1 and 3A, the apparatus includes a light source 101 for generating light, a spatial light modulator ("SLM") 108, instead of a mask, for forming an optical image to be projected onto a biochip 130, a distortion correction device 110 for correcting distortion of the optical image, a reaction chamber 120 in which a base reaction for fabricating the biochip 130 occurs, and a photodetector 113 for detecting the optical image to be projected onto the biochip 130 in the reaction chamber 120.

In one exemplary embodiment, the SLM 108 is formed of an array of a plurality of micro pixels, and each pixel therein may be turned on or off, thereby selectively transmitting or reflecting light. A transmissive SLM selectively transmits or blocks light in pixels of the transmissive SLM and a reflective SLM selectively reflects or absorbs light in pixels of the reflective SLM. Thus, an optical image to be projected onto the biochip 130 may be formed without using a mask, by controlling the on/off state of each pixel in the SLM 108. For example, in one exemplary embodiment a liquid crystal device may be used as the transmissive SLM. Also, in alternative embodiments a liquid crystal on silicon ("LCoS") or an array of micromirrors according to a micro electro mechanical system ("MEMS") technology, e.g., a digital micromirror device ("DMD"), may be used as the reflective SLM.

Meanwhile, in one exemplary embodiment, a nonlinear optical medium on which a plurality of patterns are previously recorded in the form of a three-dimensional ("3D") array based on a hologram method may be used as the SLM 108. The nonlinear optical medium may be formed to create different optical images by varying diffraction conditions of incident light based on an incident angle, a wavelength, a focusing depth, or the like of the incident light. Such a nonlinear optical medium may be obtained by sequentially projecting different interference patterns onto the nonlinear optical medium. If the nonlinear optical medium is used, although an optical image that is not previously defined cannot be arbitrarily obtained, mask images to be used to fabricate the biochip 130 may be previously stored in the nonlinear optical medium and a required image may be extracted by varying the incident angle, the wavelength, the focusing depth, or the like of the incident light. Such a nonlinear optical medium is referred to as a type of transmissive SLM.

The reaction chamber 120 encapsulates the biochip 130 and a reaction material (e.g., a deoxyribonucleic acid ("DNA") base to be combined with the biochip 130) to be sealed from an external environment. In one exemplary embodiment, a transparent window 125 is formed on a light incident surface of the reaction chamber 120 so that light may enter or leave the reaction chamber 120. However, the transparent window 125 of the reaction chamber 120 or bio-chip 130 may distort an optical image. In addition, the optical image may also be distorted when light is reflected on or transmitted through the SLM 108 or may be distorted due to other various optical devices. The distortion correction device 110 prevents and corrects distortion of the optical image to be provided to the biochip 130 in the reaction chamber 120. In one exemplary embodiment, the distortion correction device 110 may be a mirror for intentionally providing inverse aberrations opposite to various aberrations existing on an optical path from the SLM 108 to the biochip 130 in the reaction chamber 120 so as to compensate for the various aberrations.

For example, in one exemplary embodiment, a deformable mirror having a reflective surface that is arbitrarily deformable due to mechanical or electrical manipulation may be used as the distortion correction device 110. The reflective surface of the deformable mirror is formed of a flexible member, and micro electrical or mechanical devices for partially deforming the reflective surface by pushing or pulling the reflective surface are arranged in the form of a two-dimensional ("2D") array on a lower surface of the reflective surface. Thus, aberrations may be intentionally provided onto a mirror surface of the deformable mirror. For example, if inverse spherical aberrations, opposite to spherical aberrations that are accumulated on the optical path from the SLM 108 to the biochip 130 in the reaction chamber 120, are provided to the deformable mirror, the spherical aberrations may be effectively corrected.

The distortion may be corrected with reference to an optical image that is reflected from the biochip 130 and is detected by the photodetector 113. For example, in one exemplary embodiment, before the base reaction is started, the SLM 108 creates an image of vertical or horizontal parallel lines, a mesh, or a checker board and provides the image to the biochip 130. The image of such a pattern is reflected from the biochip 130 and is detected by the photodetector 113. In this exemplary embodiment, the mirror surface of the deformable mirror may be manipulated such that the image detected by the photodetector 113 is identical to the image created by the SLM 108.

After the distortion is corrected, the fabricating of the biochip 130 may be started by providing a reaction material in the reaction chamber 120 and projecting light onto the biochip 130 at the same time. In this exemplary embodiment, the photodetector 113 may verify whether an undistorted optical image is provided to the biochip 130 by continuously monitoring the optical image that is provided to the biochip 130.

Figure 2:
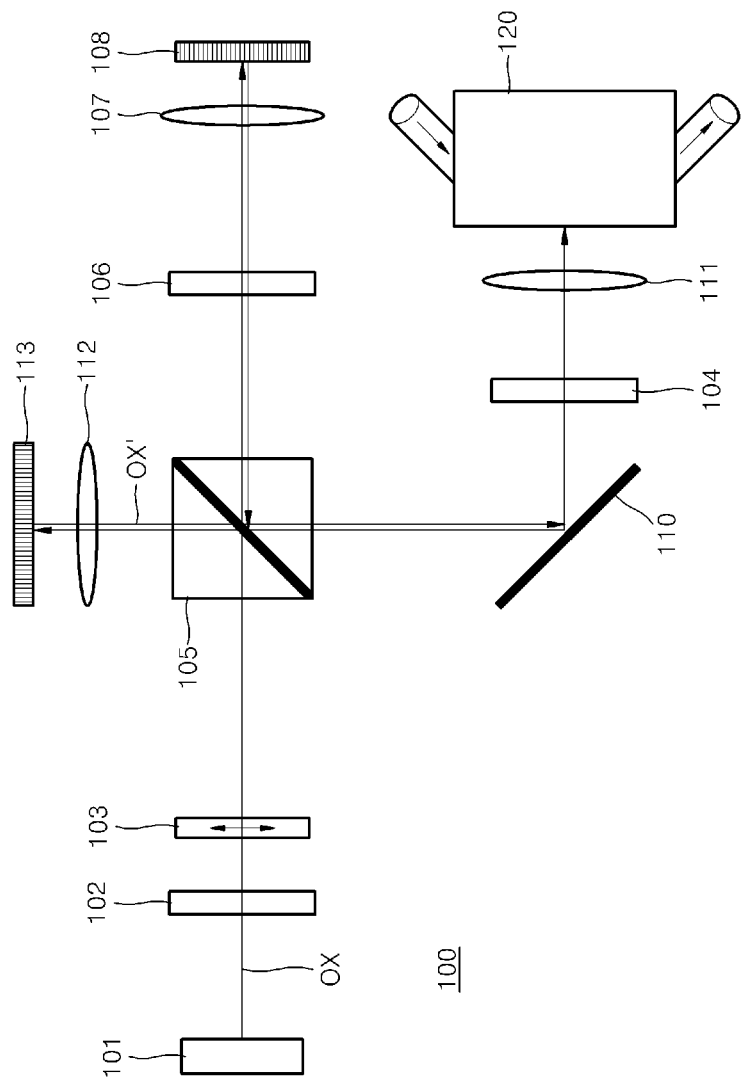
FIG. 2 is a detailed diagram of an exemplary embodiment of the apparatus illustrated in FIG. 1.

FIG. 2 is a detailed diagram of an apparatus 100 for fabricating a biochip without using a mask, according to an exemplary embodiment is illustrated.

Referring to FIG. 2, the apparatus 100 sequentially includes a light source 101, a light diffusion device 102, a polarizer 103, a polarizing beam splitter 105, a quarter-wavelength ("λ/4") plate 106, a lens device 107, and an SLM 108 in a direction where light proceeds along a first optical axis OX. Also, the apparatus 100 sequentially includes a photodetector 113, an imaging lens 112, the polarizing beam splitter 105, a distortion correction device 110, a λ/4 plate 104, a projection optical system 111, and a reaction chamber 120 along a second optical axis OX'. The polarizing beam splitter 105 is disposed on the first and second optical axes OX and OX'. The light source 101, the light diffusion device 102, the lens device 107, the SLM 108, the distortion correction device 110, and the projection optical system 111 form an exposure system for exposing a biochip 130, shown in FIG. 3A which will be fabricated in the reaction chamber 120. Also, the imaging lens 112 and the photodetector 113 may be utilized to form a monitoring system for monitoring a process of fabricating the biochip 130 in real time. In addition, the polarizer 103, the polarizing beam splitter 105, and the λ/4 plates 106 and 104 may be utilized to form an optical path changing unit for changing an optical path.

Although the above descriptions have been presented on the assumption that each of optical systems according the above exemplary embodiments are refractive optical systems that include a lens or lenses, the same functions and effects may be achieved in a reflective optical system including a flat mirro, a concave mirror or a convex mirror. For example, in one exemplary embodiment a mirror device and an imaging mirror may be respectively used instead of the lens device 107 and the imaging lens 112 to be described later. Also, a catadioptric optical system including both a refractive lens and a reflective mirror may be used. In the following description, for convenience of explanation, the refractive optical system will be representatively described.

According to the current exemplary embodiment, the light source 101 of the exposure system emits exposure light to be projected onto the biochip 130 to be fabricated. The exposure light may be coherent light or incoherent light for example. A light source for emitting light having a short wavelength (e.g., ultraviolet ("UV") light) is advantageous in order to obtain an optical image having a relatively high resolution. However, the light source 101 is not limited thereto. Every type of a light source used in a general photolithographic apparatus may be used as the light source 101. A light emitting diode ("LED") or a laser diode ("LD") for emitting monochromatic light, or a lamp for emitting white light or mixed color light may be used. For example, a mercury lamp, a deuterium ($D_2$) lamp, or a xenon (Xe) lamp, or other lamps with similar operational characteristics, may be used as the light source 101.

The exposure light emitted from the light source 101 may be transmitted through the light diffusion device 102. The light diffusion device 102 uniformly diffuses the exposure light so that substantially an entire cross section of the exposure light has uniform intensity. Thus, the exposure light may be projected with the same intensity onto the biochip 130 to be fabricated, which guarantees that a base is accurately combined with a desired gene spot on the biochip 130. Although the light diffusion device 102 is schematically illustrated as a single flat-panel device in FIG. 2, the light diffusion device 102 may be formed in various forms. For example, in alternative exemplary embodiments, the light diffusion device 102 may be a bar-type optical integrator, a diffraction lattice, a micro lens, or a diffuser. Also, the light diffusion device 102 may be formed of a plurality of optical devices in order to improve light uniformity.

Meanwhile, although the light source 101 and the light diffusion device 102 are disposed on the first optical axis OX together with other optical devices in FIG. 2, when an appropriate optical transfer means, e.g., an optical fiber (not shown) is used, the light source 101 and the light diffusion device 102 may be disposed outside of the first optical axis OX in alternative exemplary embodiments. If the optical fiber is used, the exposure light emitted from the light source 101 may be sufficiently and uniformly diffused while proceeding through the optical fiber and thus the light diffusion device 102 may be omitted. If the optical fiber is used, a degree of design freedom in an arrangement of the light source 101 may be increased and thus an amount of effort for arranging the light source 101 may be decreased.

The polarizer 103 is disposed next to the light diffusion device 102. The polarizer 103 makes the exposure light to have a specific polarization. For example, light transmitted through the polarizer 103 may be S-polarized light. However, if the light source 101 is designed to emit light having a specific polarization, the polarizer 103 may not be used. For example, if the light source 101 is a laser for emitting S-polarized light, the polarizer 103 may not be used.

The polarizing beam splitter 105 is disposed next to the polarizer 103. The polarizing beam splitter 105 transmits or blocks incident light based on the polarization of the incident light. For example, in one exemplary embodiment, the polarizing beam splitter 105 may transmit S-polarized light and reflect P-polarized light. By using the polarizing beam splitter 105, the exposure light emitted from the light source 101 may proceed toward the SLM 108 and light reflected from the SLM 108 may proceed toward the reaction chamber 120. Thus, the polarizing beam splitter 105 may be referred to as an optical path changing device. As described above, the polarizing beam splitter 105 forms the optical path changing unit, together with the polarizer 103, and the λ/4 plates 106 and 104, which will be described in greater detail below. In FIG. 2, the exposure light emitted from the light source 101 is transmitted through the polarizing beam splitter 105 and proceeds toward the SLM 108, and the light reflected from the SLM 108 is reflected on the polarizing beam splitter 105. However, in an alternative embodiment, the exposure light emitted from the light source 101 may be reflected on the polarizing beam splitter 105 and the light reflected from the SLM 108 may be transmitted through the polarizing beam splitter 105. In this exemplary embodiment, the distortion correction device 110, the λ/4 plate 104, the projection optical system 111, and the reaction chamber 120 would be disposed on the first optical axis OX, instead of the λ/4 plate 106, the lens device 107, and the SLM 108.

Light transmitted through the polarizing beam splitter 105 is transmitted through the λ/4 plate 106. The λ/4 plate 106 converts linearly polarized light into circularly polarized light, or vice versa. For example, in one exemplary embodiment, S-polarized light that is incident on the λ/4 plate 106 may be converted into left-hand circularly polarized light.

Then, the left-hand circularly polarized light is incident on the SLM 108 through the lens device 107. In this exemplary embodiment, a special lens such as an aspherical lens may be used as the lens device 107 in order to minimize the influence of aberrations.

Although the lens device 107 is formed of a single lens device in FIG. 2, in alternative exemplary embodiments, the lens device 107 may be formed of a lens group including a plurality of lenses. In this exemplary embodiment, at least one lens from the lens group may be an aspherical lens. Meanwhile, the SLM 108 according to the current exemplary embodiment is a reflective SLM. For example, an LCOS or a DMD may be used as the SLM 108. The SLM 108 reflects some of incident light and absorbs or deflects the other portion of the incident light outside of the optical path, based on a light pattern to be provided to the biochip 130 in the reaction chamber 120. Thus, the light reflected from the SLM 108 forms an optical image having a predetermined pattern.

The light reflected from the SLM 108 has an inverse circular polarization. For example, in one exemplary embodiment, the left-hand circularly polarized light is converted into right-hand circularly polarized light, and then is retransmitted through the λ/4 plate 106. In this exemplary embodiment, the light is converted into, for example, P-polarized light by the λ/4 plate 106. Then, the P-polarized light is reflected on the polarizing beam splitter 105 and proceeds toward the distortion correction device 110. As described above with reference to FIG. 1, the distortion correction device 110 prevents and corrects distortion of the optical image to be provided to the biochip 130 in the reaction chamber 120. For example, the distortion correction device 110 may be a mirror for intentionally providing inverse aberrations opposite to various aberrations existing on the optical path from the SLM 108 to the biochip 130 in the reaction chamber 120 so as to compensate for the various aberrations. For example, a deformable mirror having a reflective surface that is arbitrarily deformable due to mechanical or electrical manipulation may be used as the distortion correction device 110.

Light reflected from the distortion correction device 110 is transmitted through the λ/4 plate 104 and then is incident on the biochip 130 in the reaction chamber 120 through the projection optical system 111. The projection optical system 111 projects the optical image with a relatively high resolution onto the biochip 130, and may be a lens system including a plurality of lenses. The optical image to be provided to the biochip 130 in the reaction chamber 120 through the projection optical system 111 has a size corresponding to an overall area of the biochip 130. In this exemplary embodiment, the optical image is focused on the biochip 130 accurately in view of the size and position corresponding to the biochip 130. In order to control the size and the position of the optical image, in one exemplary embodiment, the projection optical system 111 may be a zoom lens system having a predetermined magnification or a variable magnification. An aspherical lens may be used as the projection optical system 111 in order to minimize the influence of aberrations. The projection optical system 111 may be formed of a lens group including a plurality of lenses. In this exemplary embodiment, at least one lens from the lens group may be an aspherical lens.

Referring to FIG. 3A, the reaction chamber 120 provides a sealed environment when the biochip 130 is fabricated. A transparent window 125 is formed on a light incident surface of the reaction chamber 120 so that light may enter or leave the reaction chamber 120. Also, an inlet 121 for providing a base for reacting with the biochip 130 and an outlet 122 for discharging the base remaining after reacting with the biochip 130 are formed on the reaction chamber 120. When the optical image having a predetermined pattern, which is formed by the SLM 108, is provided to the biochip 130, only an exposed portion of the biochip 130 is combined with the base. Thus, according to the current exemplary embodiment, a specific base may be combined with a desired portion of the biochip 130 without using a mask.

Referring to FIG. 2, the monitoring system including the imaging lens 112 and the photodetector 113 is disposed to face one of light exit surfaces of the polarizing beam splitter 105 in order to detect the optical image that is reflected from the biochip 130 in the reaction chamber 120 and is transmitted through the polarizing beam splitter 105. Thus, light reflected from the biochip 130 is retransmitted through the projection optical system 111 and the λ/4 plate 104. In this exemplary embodiment, the light is converted, for example, from P-polarized light into S-polarized light. Then, the light is passed through the distortion correction device 110 and the polarizing beam splitter 105 and forms an image on the photodetector 113 by the imaging lens 112. The photodetector 113 may monitor the optical image that is provided to the biochip 130 in real time. Thus, according to the current exemplary embodiment, the photodetector 113 may verify whether an accurate image pattern is provided to the biochip 130. As such, an error may be corrected in real time by getting feedback between the photodetector 113 and the SLM 108, utilizing a computer operably coupled to both the photodetector 113 and the SLM 108. The photodetector 113 may be formed of an array of several hundred thousand micro pixels to several hundred million micro pixels. For example, a photomultiplier tube ("PMT"), a charge-coupled device ("CCD"), or a complementary metal-oxide-semiconductor ("CMOS") image sensor ("CIS") may be used as the photodetector 113.

FIGS. 3A-3D are sequential diagrams showing a process of fabricating a biochip 130 by using the apparatus 100 illustrated in FIG. 2, according to another exemplary embodiment. FIGS. 3A-3D will be described in conjunction with FIG. 2.

Referring to FIG. 3A, the biochip 130 to be fabricated is disposed in the reaction chamber 120. A transparent window 125 on which exposure light is incident is formed on an upper surface of the reaction chamber 120. Furthermore, an inlet 121 for providing a base for reacting with the biochip 130 and an outlet 122 for discharging the base remaining after reacting with the biochip 130 are formed on both sides of the reaction chamber 120. In FIG. 3A, in one exemplary embodiment, only four gene spots 126 are arranged on the biochip 130. Furthermore, a photolabile material 127 is combined with each of the gene spots 126.

Figure 3B:
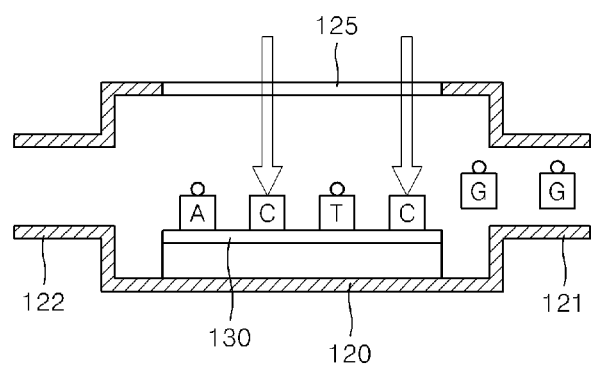
Figure 3C:
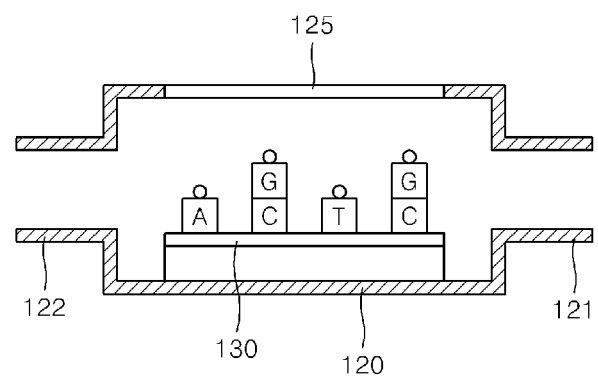

Referring to FIG. 3B, during operation, if an exposure system including the SLM 108 projects light onto only the second and fourth gene spots, the photolabile material 127 that is combined with the second and fourth gene spots is removed. Simultaneously or sequentially, if the base is provided into the reaction chamber 120 through the inlet 121, the base is combined with only the gene spots from which the photolabile material 127 is removed. Then, as illustrated in FIG. 3C, guanine (G) is newly stacked on the second and fourth gene spots. The photolabile material 127 is also combined with the newly stacked G.

Figure 3D:
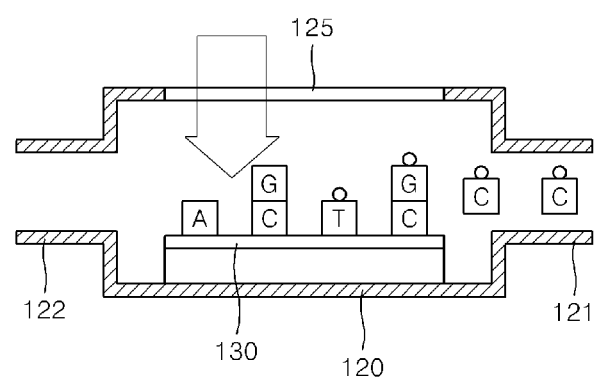
Figure 3E:
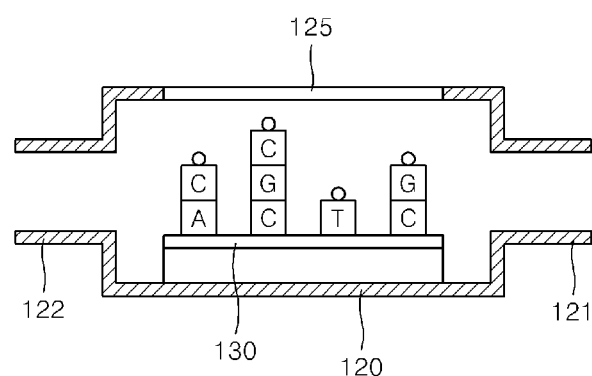

Then, referring to FIG. 3D, the exposure system projects light onto the first and second gene spots while cytosine (C) is being provided into the reaction chamber 120 through the inlet 121. Then, the photolabile material 127 is removed from the first and second gene spots. Thus, as illustrated in FIG. 3E, C is stacked on only the first and second gene spots. In this manner, a specific base may be combined with desired gene spots on the biochip 130 by exposing the biochip 130 to a predetermined image pattern and then providing the specific base into the reaction chamber 120. Desired base sequences may be created in the biochip 130 by repeating the above procedure.

According to the current exemplary embodiment, due to the SLM 108, the biochip 130 may be fabricated by using a photolithographic method without using a mask at all. Thus, designing, fabricating, inspecting, and disposing of masks may be omitted and fabricating cost and time of the biochip 130 may be reduced. Also, since the exposure system for reacting bases with the biochip 130 and exposing the biochip 130 in the reaction chamber 120 exists outside the reaction chamber 120, reduction of a yield rate of the biochip 130, which is caused by influence of, for example, humidity and ozone ($O_3$), may be prevented. Also, distortion of an optical image, which occurs on an optical path between the SLM 108 and the reaction chamber 120, may be corrected by using the projection optical system 111 such as a deformable mirror, which is described above with reference to FIG. 2. Furthermore, a process of fabricating the biochip 130 may be monitored in real time by using the photodetector 113 and thus the biochip 130 may be very accurately fabricated.

Figure 4:
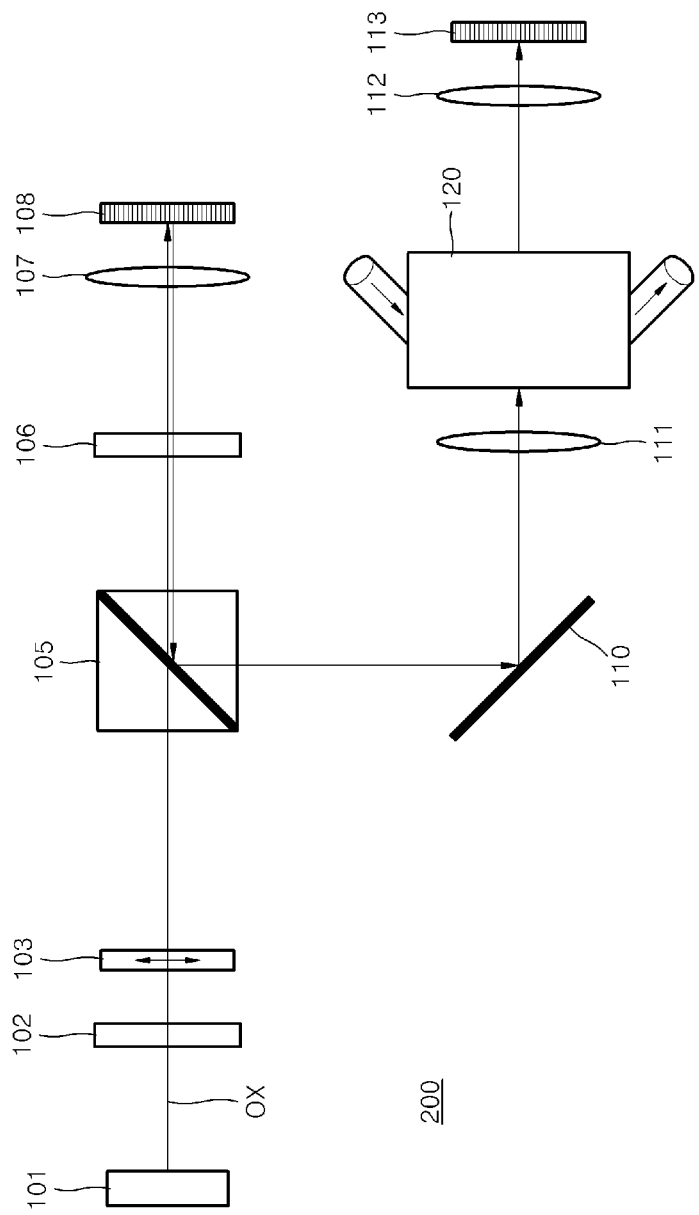
FIG. 4 is a schematic diagram of another exemplary embodiment of an apparatus for fabricating a biochip.

FIG. 4 is a schematic diagram of an apparatus 200 for fabricating a biochip, according to another exemplary embodiment. FIG. 4 will be described in conjunction with FIG. 2.

Referring to FIG. 4, the apparatus 200 is different from the apparatus 100 illustrated in FIG. 2 in that the imaging lens 112 and the photodetector 113 are disposed next to the reaction chamber 120 along a direction where light proceeds. The other configuration and operation of the apparatus 200 are substantially similar to those of the apparatus 100 illustrated in FIG. 2. However, the $\lambda/4$ plate 104 illustrated in FIG. 2 is not required to be disposed on an optical path between the distortion correction device 110 and the reaction chamber 120. According to the current exemplary embodiment, the transparent window 125 illustrated in FIG. 3A is formed on each of front and rear surfaces of the reaction chamber 120 in order to dispose the imaging lens 112 and the photodetector 113 next to the reaction chamber 120. Also, a substrate of the biochip 130 illustrated in FIG. 3A which will be fabricated in the reaction chamber 120 is formed of a transparent material. As such, an optical image that is projected onto the biochip 130 through the front surface of the reaction chamber 120, may form an image on the photodetector 113 through the substrate of the biochip 130, the rear surface of the reaction chamber 120, and the imaging lens 112. Selectively, the imaging lens 112 may be omitted and the photodetector 113 may be directly attached on the rear surface of the reaction chamber 120 or be disposed proximate to the rear surface of the reaction chamber 120.

Figure 5:
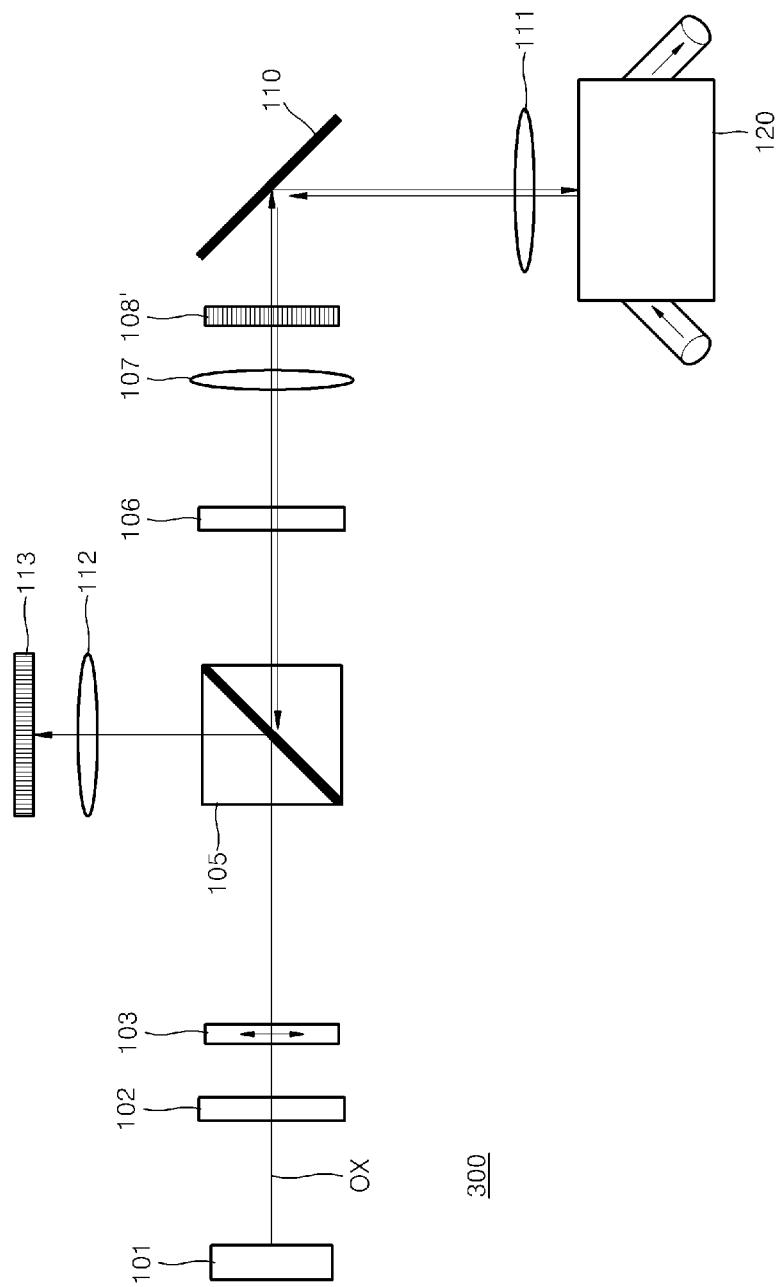
FIG. 5 is a schematic diagram of another exemplary embodiment of an apparatus for fabricating a biochip.

FIG. 5 is a schematic diagram of an apparatus 300 for fabricating a biochip, according to another exemplary embodiment. FIG. 5 will be described in conjunction with FIG. 2.

Referring to FIG. 5, the apparatus 300 is different from the apparatus 100 illustrated in FIG. 2 in that an SLM 108' is a transmissive SLM instead of a reflective SLM. Thus, for example, in one exemplary embodiment, a liquid crystal device or a nonlinear optical medium may be used as the SLM 108'. The liquid crystal device or the nonlinear optical medium may have a plurality of patterns previously recorded thereon in the form of a 3D array based on a hologram method. Since the transmissive SLM is used as the SLM 108' in the current exemplary embodiment, the light source 101, the light diffusion device 102, the polarizer 103, the polarizing beam splitter 105, the $\lambda/4$ plate 106, the lens device 107, the SLM 108', the distortion correction device 110, the projection optical system 111, and the reaction chamber 120 may be sequentially disposed on a single common optical axis OX that is folded by the distortion correction device 110. According to the current exemplary embodiment, an optical path changing unit including the polarizer 103, the polarizing beam splitter 105, and the $\lambda/4$ plate 106 provides light emitted from the light source 101 to the reaction chamber 120 and provides light reflected from the reaction chamber 120 to a monitoring system including the imaging lens 112 and the photodetector 113.

In the apparatus 300 illustrated in FIG. 5, light is emitted from the light source 101, is transmitted through the SLM 108' which forms an optical image. The light transmitted through the SLM 108' may be reflected on the distortion correction device 110 disposed next to the SLM 108'. The distortion correction device 110 may project the received light onto the biochip 130 illustrated in FIG. 3A in the reaction chamber 120 through the projection optical system 111. Meanwhile, light reflected from the biochip 130 proceeds backward along the above path. In more detail, the light reflected from the biochip 130 is transmitted through the projection optical system 111, the distortion correction device 110, the SLM 108', the lens device 107, and the λ/4 plate 106. In this exemplary embodiment, the λ/4 plate 106 changes the polarization of the light. Thus, in the current exemplary embodiment, the light reflected from the biochip 130 may be reflected on the polarizing beam splitter 105 and may form an image on the photodetector 113 through the imaging lens 112. Another distortion correction device 110 may be disposed in between the polarizing beam splitter 105 and the photodetector 113, to correct optical distortion in the beam path after the biochip 130.

Figure 6:
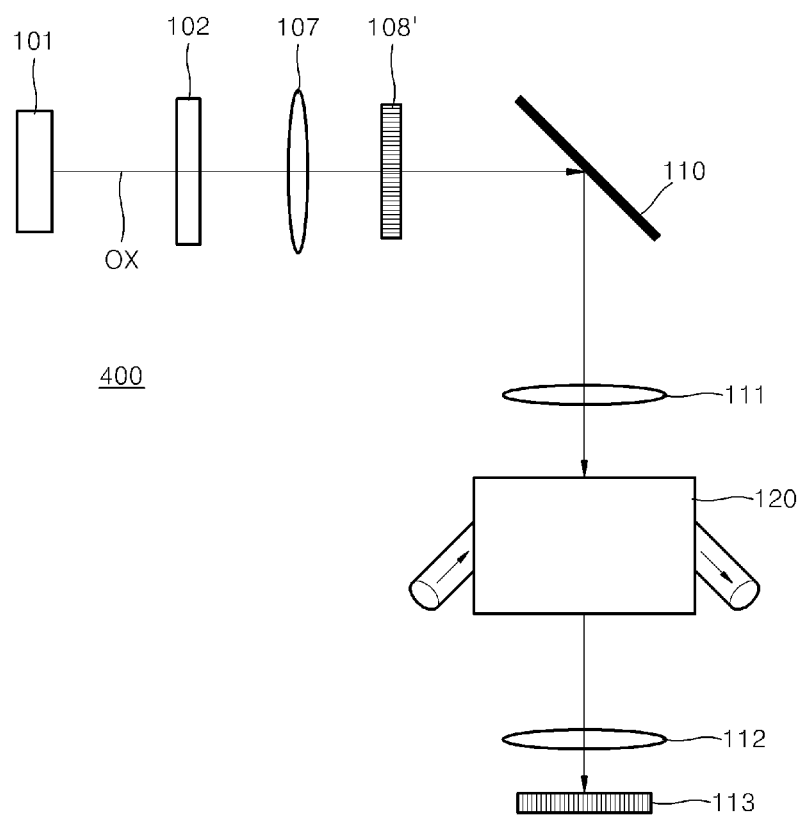
FIG. 6 is a schematic diagram of another exemplary embodiment of an apparatus for fabricating a biochip.

FIG. 6 is a schematic diagram of an apparatus 400 for fabricating a biochip, according to another exemplary embodiment. FIG. 6 will be described in conjunction with FIGS. 4 and 5.

Referring to FIG. 6, the apparatus 400 is different from the apparatus 300 illustrated in FIG. 5 in that the imaging lens 112 and the photodetector 113 are disposed next to the reaction chamber 120. Also, according to the current exemplary embodiment, since light emitted from the light source 101 is not required to proceed backward along an original path or be divided along different paths while the light proceeds from the light source 101 toward the photodetector 113 through the biochip 130 illustrated in FIG. 3A, an optical path changing unit is not required. Thus, the polarizer 103, the polarizing beam splitter 105, and the λ/4 plates 106 which are used in the previous exemplary embodiments are not required in the current exemplary embodiment.

As in the apparatus 300 illustrated in FIG. 5, the apparatus 400 also uses the SLM 108' that is a transmissive SLM instead of a reflective SLM. Thus, for example, a liquid crystal device or a nonlinear optical medium on which a plurality of patterns are previously recorded in the form of a 3D array based on a hologram method, may be used as the SLM 108'. The operation of the apparatus 400 is substantially similar to that of the apparatus 300 illustrated in FIG. 5.

As in the apparatus 200 illustrated in FIG. 4, in the apparatus 400, the imaging lens 112 and the photodetector 113 are disposed next to the reaction chamber 120. Furthermore, the transparent window 125 illustrated in FIG. 3A is formed on each of front and rear surfaces of the reaction chamber 120. Also, a substrate of the biochip 130 to be fabricated in the reaction chamber 120 is formed of a transparent material. As such, an optical image that is projected onto the biochip 130 through the front surface of the reaction chamber 120 may form an image on the photodetector 113 through the substrate of the biochip 130, the rear surface of the reaction chamber 120, and the imaging lens 112. Selectively, as described above with reference to FIG. 4, the imaging lens 112 may be omitted and the photodetector 113 may be directly attached on the rear surface of the reaction chamber 120 or be disposed proximate to the rear surface of the reaction chamber 120.

Meanwhile, in order to directly analyze a sample by using the biochip 130 that is fabricated in the reaction chamber 120 without carrying the biochip 130 out of the reaction chamber 120, an apparatus for both fabricating and optically detecting a biochip, may be provided.

Figure 7:
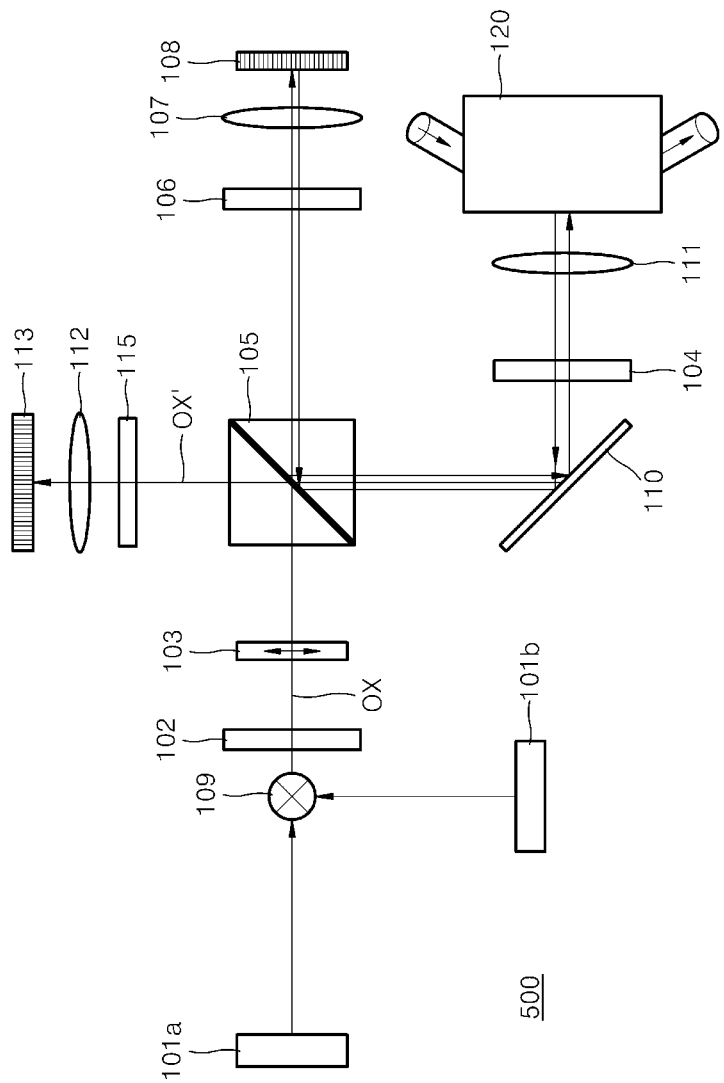
FIG. 7 is a schematic diagram of another exemplary embodiment of an apparatus for fabricating and optically detecting a biochip.

FIG. 7 is a schematic diagram of an apparatus 500 for fabricating and optically detecting a biochip, which is capable of both fabricating the biochip and analyzing a sample, according to another exemplary embodiment.

Referring to FIG. 7, the apparatus 500 includes first and second light sources 101a and 101b, an optical multiplexer 109, a light diffusion device 102, a polarizer 103, a polarizing beam splitter 105, λ/4 plates 106 and 104, a lens device 107, an SLM 108, a photodetector 113, an imaging lens 112, an excitation light absorption filter 115, a distortion correction device 110, a projection optical system 111, and a reaction chamber 120. In one exemplary embodiment, the optical multiplexer 109, the light diffusion device 102, the polarizer 103, the polarizing beam splitter 105, the λ/4 plate 106, the lens device 107, and the SLM 108 are sequentially disposed in a direction in which light proceeds along a first optical axis OX. Also, the photodetector 113, the imaging lens 112, the excitation light absorption filter 115, the polarizing beam splitter 105, the distortion correction device 110, the λ/4 plate 104, the projection optical system 111, and the reaction chamber 120 are sequentially disposed along a second optical axis OX'. The polarizing beam splitter 105 is disposed on the first and second optical axes OX and OX'.

The first and second light sources 101a and 101b, the optical multiplexer 109, the light diffusion device 102, the lens device 107, the SLM 108, the distortion correction device 110, and the projection optical system 111 form an exposure system for exposing the biochip 130 illustrated in FIG. 3A, which will be fabricated in the reaction chamber 120, and for projecting excitation light onto the biochip 130 when the sample is analyzed. Also, the excitation light absorption filter 115, the imaging lens 112, and the photodetector 113 form a monitoring and fluorescent light detection system for monitoring a process of fabricating the biochip 130 in real time and for detecting fluorescent light emitted from the biochip 130. In addition, the polarizer 103, the polarizing beam splitter 105, and the λ/4 plates 106 and 104 form an optical path changing unit for changing an optical path. For example, the optical path changing unit provides exposure light emitted from the first light source 101a, to the SLM 108, and light reflected from the SLM 108 is directed to the reaction chamber 120. Also, the optical path changing unit provides excitation light emitted from second light source 101b, to the reaction chamber 120. Light reflected from the biochip 130 or fluorescent light emitted from the biochip 130 in the reaction chamber 120 proceeds toward the photodetector 113 through the optical path changing unit.

As described above in FIG. 2, although the above descriptions have been presented on an assumption that each of optical systems according the current exemplary embodiment and other exemplary embodiments to be described later is a refractive optical system that includes a lens or lenses, the similar functions and effects may be achieved in a reflective optical system including a flat mirror, a concave mirror or a convex mirror.

According to the current exemplary embodiment, the first light source 101a of the exposure system emits exposure light to be projected onto the biochip 130 to be fabricated. The exposure light has been described above with reference to FIG. 2 and thus detailed descriptions thereof will be omitted. Meanwhile, the second light source 101b emits excitation light. The excitation light excites fluorescent materials included in sample genes combined with spots in the biochip 130 (e.g., a DNA chip). In general, UV light, visible light, or infrared light may be used as the excitation light. Further, in one exemplary embodiment, the excitation light has a wavelength of, for example, about 500 nm. However, the excitation light does not need to be light having a wavelength of about 500 nm and light having a spectrum band including a wavelength of about 500 nm may be used as the excitation light. Further, the excitation light does not need to be monochromatic light. Also, the wavelength of the excitation light may vary based on light emitting characteristics of the fluorescent materials combined with the sample genes. For example, a lamp for emitting mixed color light including a wavelength band of about 500 nm or an LED or an LD for emitting monochromatic light having a wavelength band of about 500 nm may be used as the second light source 101b. Furthermore, the excitation light may be coherent light or incoherent light.

The optical multiplexer 109 provides the exposure light emitted from the first light source 101a and the excitation light emitted from the second light source 101b to the same optical path along the first optical axis OX. For example, the optical multiplexer 109 may selectively transmit the exposure light emitted from the first light source 101a and block the excitation light emitted from the second light source 101b, based on an electrical signal, or vice versa. However, in general operation of the apparatus 500, only one of the first and second light sources 101a and 101b is turned on and the other is turned off, and thus the optical multiplexer 109 may simply provide incident light in the optical path along the first optical axis OX.

Initially, a case when the first light source 101a is turned on and the second light source 101b is turned off, and the exposure light from the first light source 101a proceeds toward the reaction chamber 120, will now be described. The exposure light emitted from the first light source 101a is transmitted through the optical multiplexer 109, the light diffusion device 102, and the polarizer 103. As described above with reference to FIG. 2, if the first light source 101a is designed to emit light having a specific polarization, the polarizer 103 may not be used. For example, if the first light source 101a is a laser for emitting S-polarized light, the polarizer 103 may not be used.

Then, the exposure light is transmitted through the polarizing beam splitter 105. For example, the polarizing beam splitter 105 may transmit S-polarized light and reflect P-polarized light. In FIG. 7, the exposure light emitted from the first light source 101a is transmitted through the polarizing beam splitter 105 so as to proceed toward the SLM 108 and the light reflected from the SLM 108 is reflected on the polarizing beam splitter 105. However, in an alternative exemplary embodiment, the exposure light emitted from the first light source 101a may be reflected on the polarizing beam splitter 105 and the light reflected from the SLM 108 may be transmitted through the polarizing beam splitter 105. In this exemplary embodiment, the λ/4 plate 106, the lens device 107, and the SLM 108 may be disposed on the second optical axis OX', and the distortion correction device 110, the λ/4 plate 104, the projection optical system 111, and the reaction chamber 120 may be disposed on the first optical axis OX.

Light transmitted through the polarizing beam splitter 105 is transmitted through the λ/4 plate 106. For example, in one exemplary embodiment, S-polarized light that is incident on the λ/4 plate 106 may be converted into left-hand circularly polarized light. Then, the circularly polarized light is incident on the SLM 108 through the lens device 107. The SLM 108 reflects some of incident light and absorbs or deflects the other portion of the incident light out of the optical path, based on a light pattern to be provided to the biochip 130 in the reaction chamber 120. Thus, the light reflected from the SLM 108 corresponds to an optical image having a predetermined pattern.

The light reflected from the SLM 108 has an inverse circular polarization. For example, in one exemplary embodiment, the left-hand circularly polarized light is converted into right-hand circularly polarized light, and then is retransmitted through the λ/4 plate 106. In this exemplary embodiment, the light is converted into, for example, P-polarized light by the λ/4 plate 106. Then, the P-polarized light is reflected on the polarizing beam splitter 105 and proceeds toward the distortion correction device 110. As described above with reference to FIG. 1, for example, a deformable mirror having a reflective surface that is arbitrarily deformable due to mechanical or electrical manipulation may be used as the distortion correction device 110. Light reflected from the distortion correction device 110 is transmitted through the λ/4 plate 104 and then is incident on the biochip 130 in the reaction chamber 120 through the projection optical system 111. As such, the exposure light may be provided to the biochip 130 in the reaction chamber 120.

Light reflected from the biochip 130 is retransmitted through the projection optical system 111 and the λ/4 plate 104. In this exemplary embodiment, the λ/4 plate 104 converts the light, for example, from P-polarized light into S-polarized light. Then, the S-polarized light is transmitted through the distortion correction device 110 and the polarizing beam splitter 105. According to the current exemplary embodiment, the monitoring and fluorescent light detection system including the excitation light absorption filter 115, the imaging lens 112, and the photodetector 113 faces one of light exit surfaces of the polarizing beam splitter 105 in order to detect the optical image that is reflected from the biochip 130 in the reaction chamber 120 and is transmitted through the polarizing beam splitter 105. Thus, the light transmitted through the polarizing beam splitter 105 forms an image on the photodetector 113 by the imaging lens 112. Accordingly, the photodetector 113 may verify whether an accurate image pattern is provided to the biochip 130.

The excitation light absorption filter 115 removes the excitation light that proceeds toward the photodetector 113 when a gene sample is analyzed. For example, in one exemplary embodiment, the excitation light absorption filter 115 may absorb a wavelength band of about 500 nm and transmit the other wavelength bands. However, the excitation light absorption filter 115 may not be used when the biochip 130 is fabricated. Thus, when the biochip 130 is fabricated, a predetermined shifter (not shown) may separate the excitation light absorption filter 115 from the second optical axis OX'.

Referring to FIG. 7, a process of analyzing a gene sample in the apparatus 500, according to another exemplary embodiment will now be described.

When the gene sample is analyzed by using the biochip 130 that is fabricated as described above, the gene sample to be analyzed is put into the reaction chamber 120 through the inlet 121 illustrated in FIG. 3A. Then, some of genes included in the gene sample are combined with corresponding gene spots on the biochip 130. Remaining genes of the gene sample, which are not combined with any gene spot on the biochip 130, are discharged through the outlet 122 illustrated in FIG. 3A.

After the non-combined genes are discharged form the outlet 122, the second light source 101b is turned on. Then, excitation light is emitted from the second light source 101b. In this exemplary embodiment, the first light source 101a is turned off when the second light source 101b is turned on. The excitation light may be incident on the biochip 130 in the reaction chamber 120 through the same path of the exposure light, which is described above. In more detail, the excitation light is incident on the SLM 108 through the light diffusion device 102, the polarizer 103, the polarizing beam splitter 105, the λ/4 plate 106, and the lens device 107. Then, the excitation light reflected from the SLM 108 is re-reflected on the polarizing beam splitter 105 through the lens device 107 and the λ/4 plate 106 and then is incident on the biochip 130 through the distortion correction device 110, the λ/4 plate 104, and the projection optical system 111. In this exemplary embodiment, the SLM 108 merely functions as a mirror without modulating the excitation light. For example, every pixel of the SLM 108 may reflect or transmit incident light without deflecting the incident light.

According to the current exemplary embodiment, the excitation light to be incident on the biochip 130 through the projection optical system 111 may have a diameter corresponding to an overall area of the biochip 130. In this exemplary embodiment, the biochip 130 may be completely excited by projecting the excitation light onto the biochip 130 once, without dividing the biochip 130 into a plurality of areas and sequentially scanning the plurality of areas. However, in an alternative embodiment, the excitation light may also have a small optical spot size and thus divided areas of the biochip 130 may be sequentially scanned. Although not shown in FIG. 7, an optical system including the exposure system or the reaction chamber 120 may be supported on a XYZ stage in order to adjust the position of the excitation light or to scan the biochip 130 with the excitation light.

When the excitation light is projected onto the biochip 130 as described above, a fluorescent material included in the genes of the gene sample combined with the gene spots is excited and emits fluorescent light. According to the current exemplary embodiment, the biochip 130 is formed on an opaque or reflective substrate. Thus, the fluorescent light emitted from the fluorescent material proceeds toward the polarizing beam splitter 105. In this exemplary embodiment, the fluorescent light is non-polarized light having no specific polarization and thus the polarizing beam splitter 105 merely functions as a half mirror with respect to the fluorescent light. Accordingly, some of the fluorescent light may proceed toward the excitation light absorption filter 115 through the polarizing beam splitter 105. The fluorescent light transmitted through the polarizing beam splitter 105 is incident on the photodetector 113 through the excitation light absorption filter 115 and the imaging lens 112.

Also, some of the excitation light projected onto the biochip 130 is reflected on the biochip 130 and then is retransmitted through the λ/4 plate 104. In this exemplary embodiment, the λ/4 plate 104 converts the excitation light into, for example, S-polarized light. Then, the excitation light that is the S-polarized light may be transmitted through the polarizing beam splitter 105 and may be incident on the excitation light absorption filter 115 that faces a light exit surface of the polarizing beam splitter 105. In this exemplary embodiment, only the fluorescent light is desired to be detected by the photodetector 113. However, the intensity of the excitation light is much greater than the intensity of the fluorescent light and thus the excitation light may disturb accurate detection of the fluorescent light. As described above, the excitation light absorption filter 115 is used to transmit only the fluorescent light and to absorb the excitation light, and may be a wavelength selective filter.

Meanwhile, the fluorescent light emitted from the biochip 130 is reflected on the distortion correction device 110 once and then is incident on the photodetector 113. When the biochip 130 is fabricated, the distortion correction device 110 is used to compensate for distortion of an optical image that is created by the SLM 108 and is incident on the biochip 130. For this functionality, a mirror surface of the distortion correction device 110 is deformed based on a distortion factor on an optical path from the SLM 108 to the biochip 130. The distortion correction device 110 now has to compensate for distortion of a fluorescent image that is created by the biochip 130 and is incident on the photodetector 113. For this functionality, the mirror surface of the distortion correction device 110 is deformed based on a distortion factor on the optical path from the biochip 130 to the photodetector 113. For example, the fluorescent image detected by the photodetector 113 may be analyzed and the mirror surface of the distortion correction device 110 may be deformed until distortion hardly exists on the fluorescent image that is incident on the photodetector 113.

In this manner, the fluorescent image may be provided to the photodetector 113 without distortion. The fluorescent image that is incident on the photodetector 113 is converted into an electrical signal by the photodetector 113 and the electrical signal is provided to an image signal processor (not shown) such as a computer. As described above with reference to FIG. 2, the photodetector 113 is formed of an array of several hundred thousand micro pixels to several ten million micro pixels. Thus, the fluorescent light emitted from each gene spot on the biochip 130 may be separately detected. Furthermore, the pixels of the photodetector 113 are matched with a plurality of gene spots on the biochip 130. For example, each pixel of the photodetector 113 may match with a fluorescent image of each gene spot on the biochip 130 in a one-to-one correspondence. However, in order to obtain more reliable data, a fluorescent image of each gene spot on the biochip 130 may match with a plurality of pixels of the photodetector 113 in a one-to-n correspondence wherein n is a natural number. In an alternative exemplary embodiment, a magnification ratio of the imaging lens 112 may be controlled so that a matching ratio between the pixels of the photodetector 113 and fluorescent images of the gene spots on the biochip 130 may be arbitrarily controlled. For example, in one exemplary embodiment, the imaging lens 112 may be a zoom lens system having a variable magnification.

According to the current exemplary embodiment, since the distortion of the fluorescent image may be sufficiently corrected by using the distortion correction device 110, an overall fluorescent image may be obtained without distortion by projecting the excitation light onto the biochip 130 once. Thus, the biochip 130 may be read and analyzed at a relatively high speed. Since the mirror surface of the distortion correction device 110 is arbitrarily deformable, although the surface of the biochip 130 is not uniformly even, image distortion caused by the uneven surface may be corrected. Accordingly, in the current exemplary embodiment, the biochip 130 may not have a uniformly even surface. Also, since the biochip 130 that is fabricated in the reaction chamber 120 may be directly used without carrying the biochip 130 out of the reaction chamber 120, influence of an external environment may be minimized and a reliability of a sample analysis may be improved.

Figure 8:
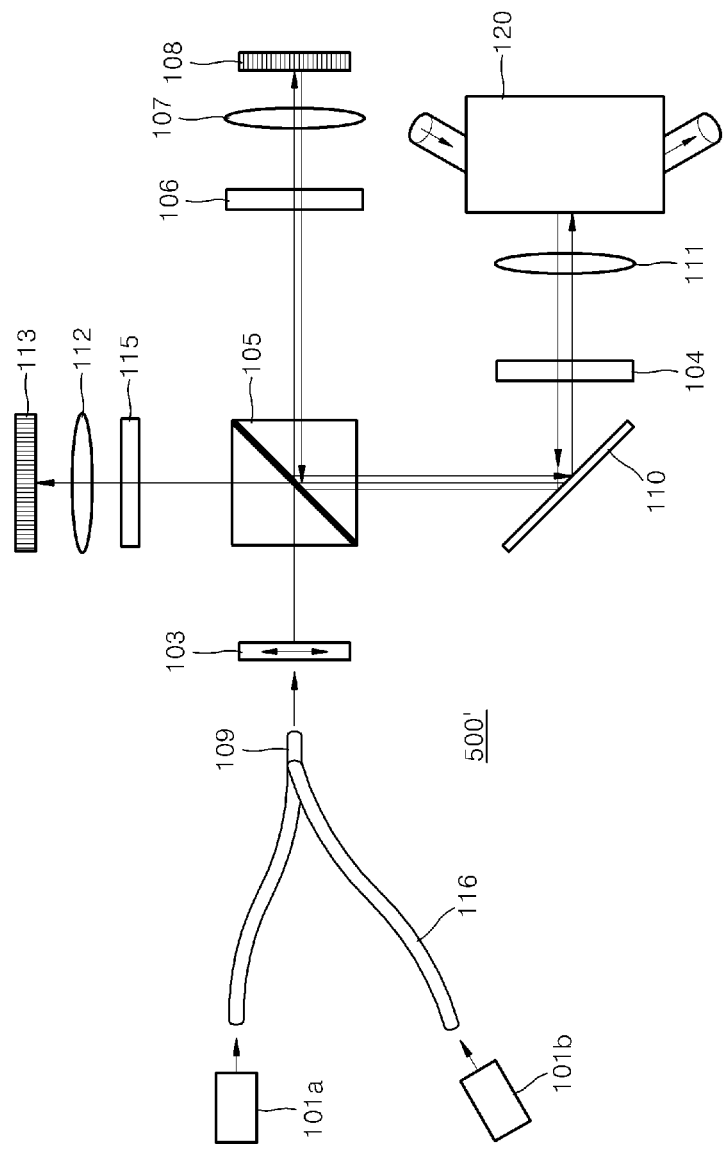
FIG. 8 is a schematic diagram of another exemplary embodiment of an apparatus for fabricating and optically detecting a biochip.

FIG. 8 is a schematic diagram of an apparatus 500' for fabricating and optically detecting a biochip, according to another exemplary embodiment. FIG. 8 will be described in conjunction with FIG. 7.

Referring to FIG. 8, an appropriate optical transfer means such as an optical fiber 116 may be disposed between the first and second light sources 101a and 101b and the optical multiplexer 109. If the optical fiber 116 is used, a degree of design freedom in the arrangement of the first and second light sources 101a and 101b may be increased and thus an amount of effort for arranging the first and second light sources 101a and 101b may be reduced. Also, if the optical fiber 116 is used, light may be sufficiently and uniformly diffused while proceeding through the optical fiber 116 and thus the light diffusion device 102 illustrated in FIG. 7 may be omitted. Furthermore, if the first and second light sources 101a and 101b emit polarized light, a polarization maintaining optical fiber may be used as the optical fiber 116. In this exemplary embodiment, the polarizer 103 may also be omitted. The other elements of the apparatus 500' are identical to corresponding elements of the apparatus 500 illustrated in FIG. 7 and thus detailed descriptions thereof will be omitted.

Figure 9:
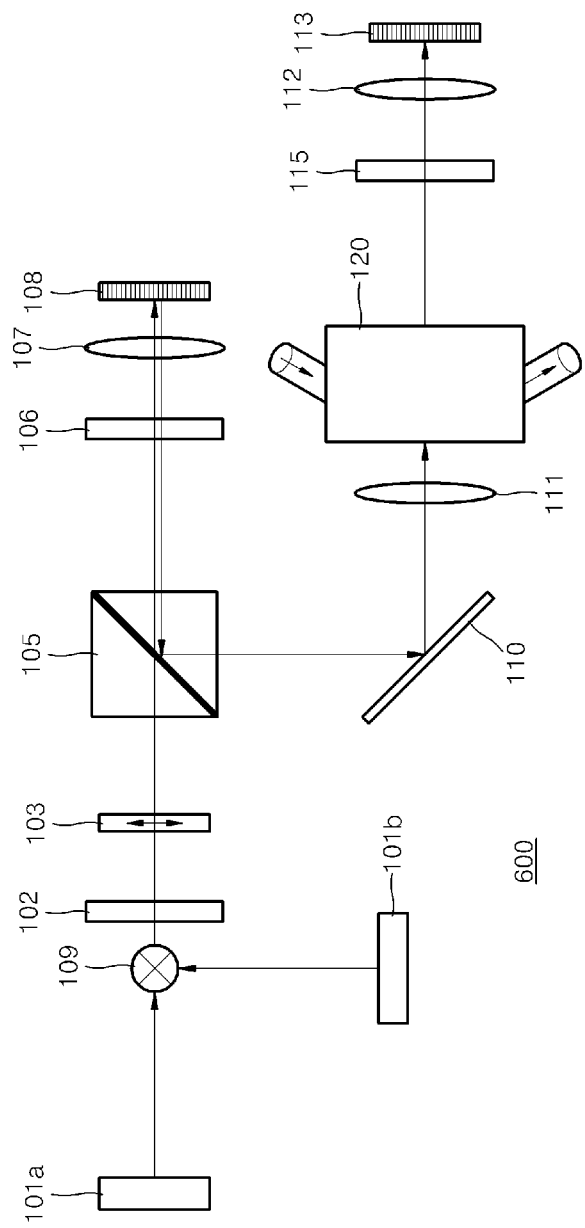
FIG. 9 is a schematic diagram of another exemplary embodiment of an apparatus for fabricating and optically detecting a biochip.
Figure 10:
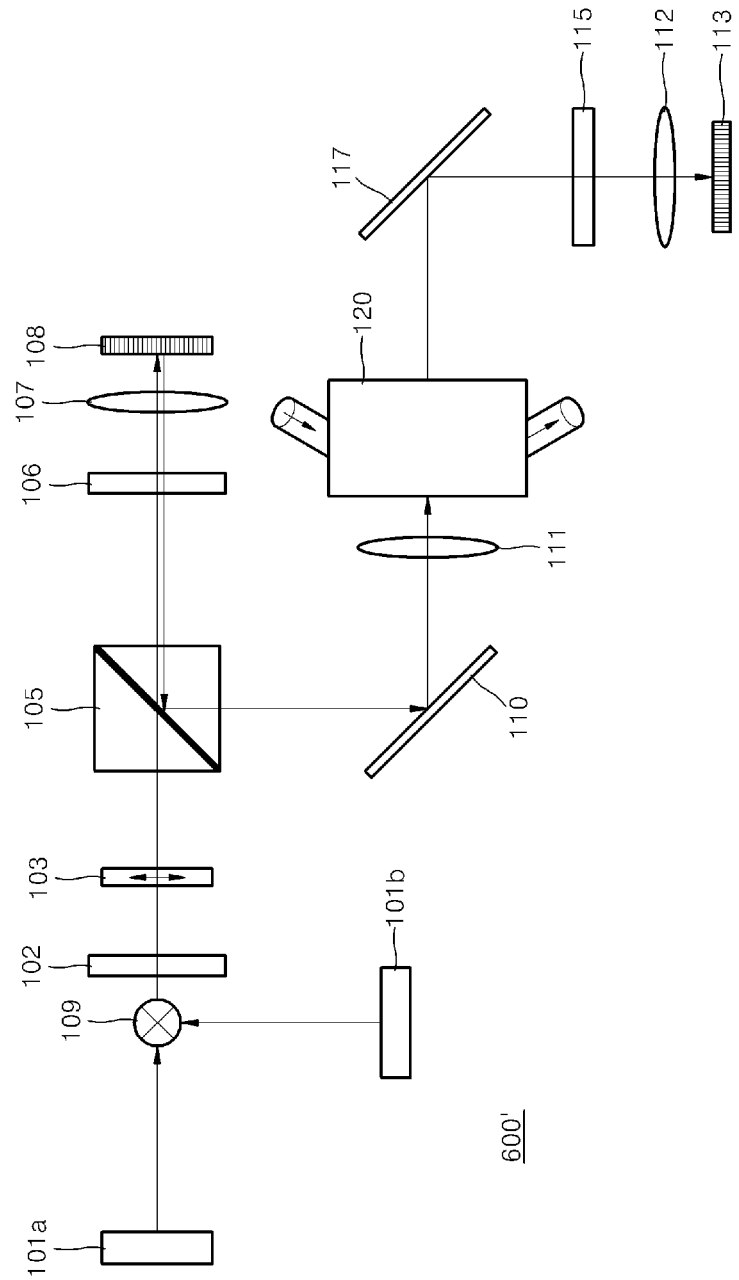
FIG. 10 is a schematic diagram of another exemplary embodiment of an apparatus for fabricating and optically detecting a biochip.

FIG. 9 is a schematic diagram of an apparatus 600 for fabricating and optically detecting a biochip, according to another exemplary embodiment. FIG. 10 is a schematic diagram of an apparatus 600' for fabricating and optically detecting a biochip, according to another exemplary embodiment. FIGS. 9 and 10 will be described in conjunction with FIG. 7.

Referring to FIG. 9, the apparatus 600 is different from the apparatus 500 illustrated in FIG. 7 in that the excitation light absorption filter 115, the imaging lens 112, and the photodetector 113 are disposed next to the reaction chamber 120 along a direction where light proceeds from the reaction chamber 120. The other configuration and operation of the apparatus 600 is substantially similar to those of the apparatus 500 illustrated in FIG. 7. However, the λ/4 plate 104 illustrated in FIG. 7 is not required to be disposed on an optical path between the distortion correction device 110 and the reaction chamber 120. According to the current exemplary embodiment, the transparent window 125 illustrated in FIG. 3A is formed on each of front and rear surfaces of the reaction chamber 120 in order to dispose the photodetector 113 next to the reaction chamber 120. Also, a substrate of the biochip 130 illustrated in FIG. 3A which will be fabricated in the reaction chamber 120 is formed of a transparent material. As such, light that is projected onto the biochip 130 through the front surface of the reaction chamber 120 may be incident on the photodetector 113 through the substrate of the biochip 130 and the rear surface of the reaction chamber 120. Selectively, the imaging lens 112 may be omitted and the excitation light absorption filter 115 and the photodetector 113 may be directly attached on the rear surface of the reaction chamber 120 or be disposed proximate to the rear surface of the reaction chamber 120.

According to the current exemplary embodiment, distortion of an optical image created by the SLM 108 when the biochip 130 is fabricated may be corrected by the distortion correction device 110. However, when the sample is analyzed, a fluorescent image created by the biochip 130 is directly incident on the photodetector 113 without correcting distortion of the fluorescent image. Thus, as illustrated in FIG. 10, a distortion correction device 117 may be added between the reaction chamber 120 and the excitation light absorption filter 115. As such, the distortion correction device 110 disposed between the polarizing beam splitter 105 and the projection optical system 111 may correct image distortion between the SLM 108 and the biochip 130. Furthermore, the distortion correction device 117 disposed between the reaction chamber 120 and the excitation light absorption filter 115 may correct image distortion between the reaction chamber 120 and the photodetector 113.

Figure 11:
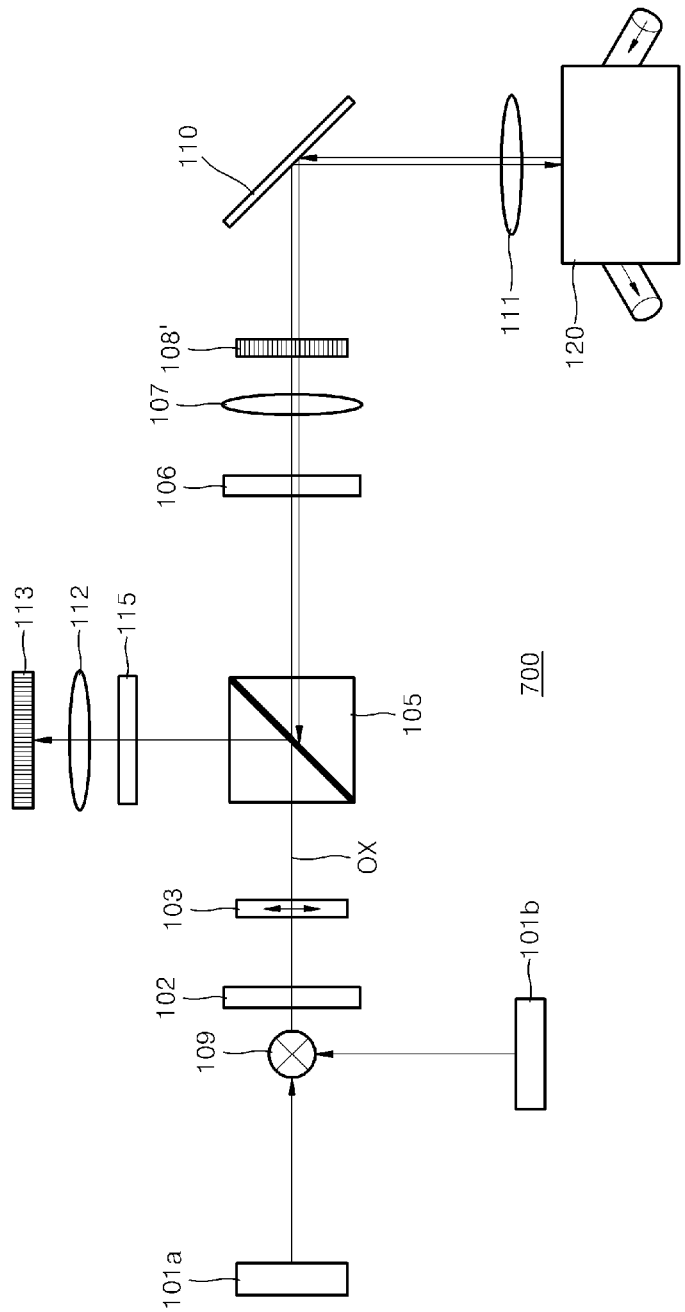
FIG. 11 is a schematic diagram of another exemplary embodiment of an apparatus for fabricating and optically detecting a biochip.

FIG. 11 is a schematic diagram of an apparatus 700 for fabricating and optically detecting a biochip, according to another exemplary embodiment. FIG. 11 will be described in conjunction with FIG. 7.

Referring to FIG. 11, the apparatus 700 is different from the apparatus 500 illustrated in FIG. 7 in that an SLM 108' is a transmissive SLM instead of a reflective SLM. Thus, for example, a liquid crystal device or a nonlinear optical medium on which a plurality of patterns are previously recorded in a form of a 3D array based on a hologram method, may be used as the SLM 108'.

Since the transmissive SLM is used as the SLM 108' in the current exemplary embodiment, the optical multiplexer 109, the light diffusion device 102, the polarizer 103, the polarizing beam splitter 105, the λ/4 plate 106, the lens device 107, the SLM 108', the distortion correction device 110, the projection optical system 111, and the reaction chamber 120 may be sequentially disposed on a single common optical axis OX that is folded by the distortion correction device 110. According to the current exemplary embodiment, an optical path changing unit including the polarizer 103, the polarizing beam splitter 105, and the λ/4 plate 106 provides light emitted from the first and second light sources 101a and 101b, to the reaction chamber 120 and provides light reflected from the reaction chamber 120, to a monitoring and fluorescent light detection system including the excitation light absorption filter 115, the imaging lens 112, and the photodetector 113.

In the apparatus 700 illustrated in FIG. 11, exposure light is emitted from the first light source 101a and is transmitted through the SLM 108' which forms an optical image. Light transmitted through the SLM 108' may be reflected on the distortion correction device 110 disposed next to the SLM 108' and then may be projected onto the biochip 130 illustrated in FIG. 3A in the reaction chamber 120 through the projection optical system 111. Meanwhile, light reflected from the biochip 130 proceeds backward along the above path. In more detail, the light reflected from the biochip 130 is transmitted through the projection optical system 111, the distortion correction device 110, the SLM 108', the lens device 107, and the λ/4 plate 106. In this exemplary embodiment, the λ/4 plate 106 changes a polarization of the light. Thus, the light reflected from the biochip 130 may be reflected on the polarizing beam splitter 105 and may be incident on the photodetector 113.

On the other hand, when a gene sample is analyzed, excitation light emitted from the second light source 101b and fluorescent light emitted from the biochip 130 are transmitted through the SLM 108' without being modulated. For this functionality, the SLM 108' may be controlled so that each pixel of the SLM 108' transmits incident light without transforming the incident light. In an alternative exemplary embodiment, a predetermined shifter (not shown) may separate the SLM 108' from the optical path when the gene sample is analyzed. In this exemplary embodiment, the lens device 107 for focusing light on the SLM 108' may also be separated from the optical path.

Figure 12:
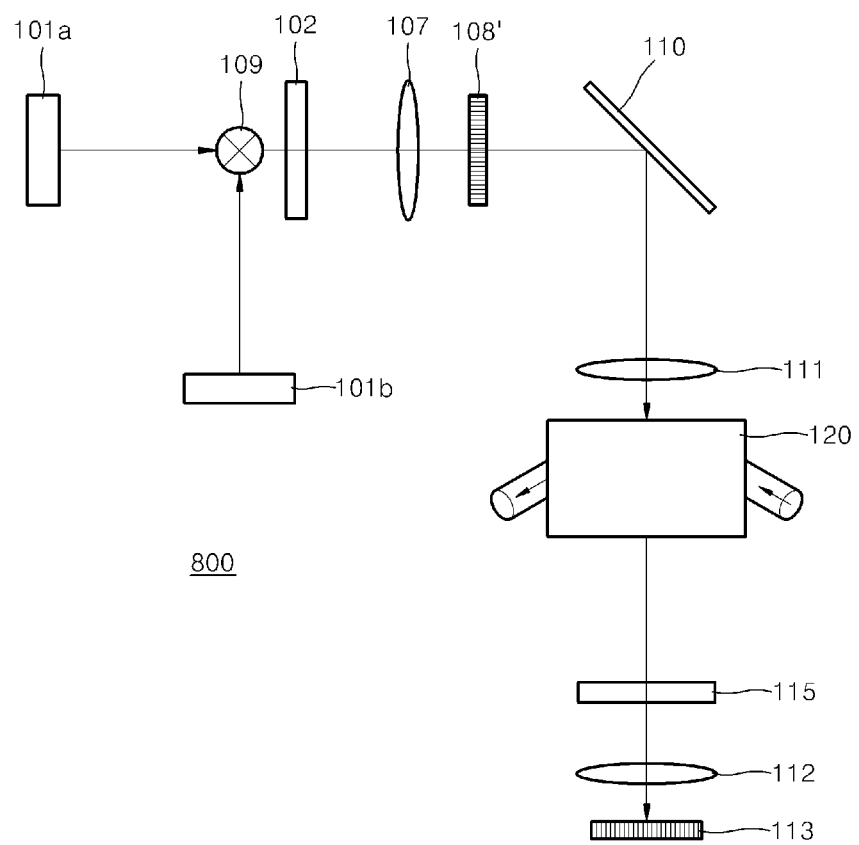
FIG. 12 is a schematic diagram of another exemplary embodiment of an apparatus for fabricating and optically detecting a biochip.
Figure 13:
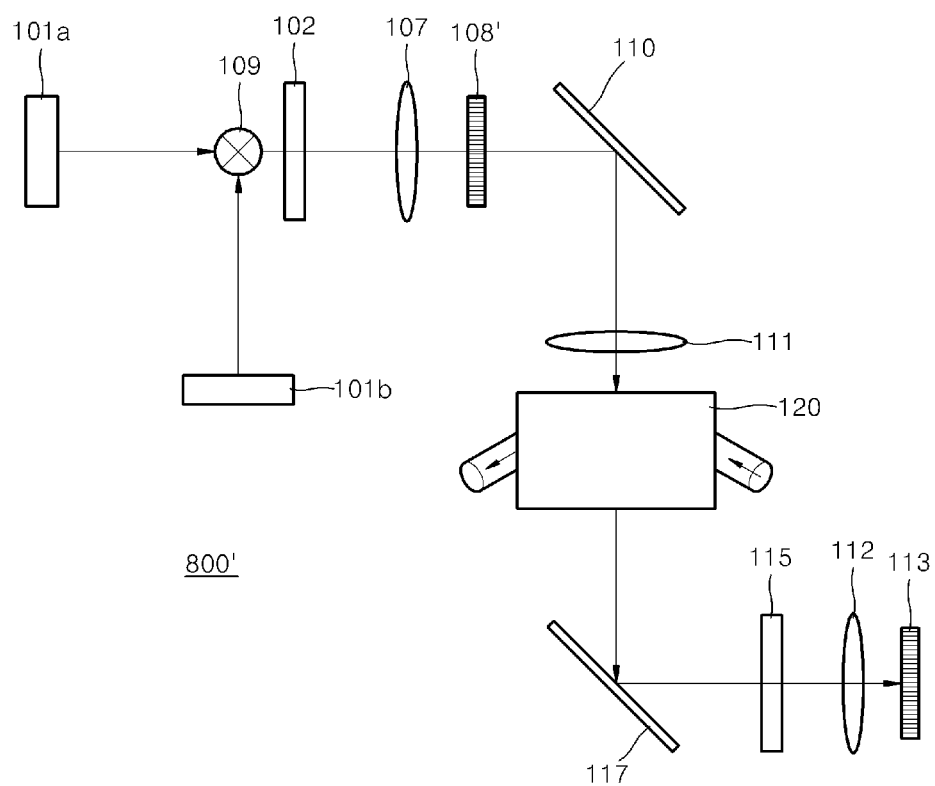
FIG. 13 is a schematic diagram of another exemplary embodiment of an apparatus for fabricating and optically detecting a biochip.

FIG. 12 is a schematic diagram of an apparatus 800 for fabricating and optically detecting a biochip, according to another exemplary embodiment. FIG. 13 is a schematic diagram of an apparatus 800' for fabricating and optically detecting a biochip, according to another exemplary embodiment. FIGS. 12 and 13 will be described in conjunction with FIGS. 7 and 11.

Referring to FIG. 12, the apparatus 800 is substantially different from the apparatus 700 illustrated in FIG. 11 in that the excitation light absorption filter 115, the imaging lens 112, and the photodetector 113 are disposed next to the reaction chamber 120. Also, according to the current exemplary embodiment, since light emitted from the first light source 101a or the second light source 101b is not required to proceed backward along an original path or to be divided along different paths while the light proceeds from the first light source 101a or the second light source 101b toward the photodetector 113 through the biochip 130 illustrated in FIG. 3A, an optical path changing unit is not required. Thus, the polarizer 103, the polarizing beam splitter 105, and the λ/4 plates 106 which are used in the previous exemplary embodiments are not required in the current exemplary embodiment.

As in the apparatus 700 illustrated in FIG. 11, the apparatus 800 also uses the SLM 108' that is a transmissive SLM instead of a reflective SLM. Thus, for example, a liquid crystal device or a nonlinear optical medium on which a plurality of patterns are previously recorded in a form of a 3D array based on a hologram method, may be used as the SLM 108'. Also, as described above with reference to FIG. 11, when a gene sample is analyzed, the SLM 108' may be controlled so that each pixel of the SLM 108' transmits incident light without transforming the incident light. In an alternative exemplary embodiment, the SLM 108' and the lens device 107 may be separated from an optical path.

Meanwhile, as in the apparatus 600 illustrated in FIG. 9, in the apparatus 800, the photodetector 113 is disposed next to the reaction chamber 120. Furthermore, the transparent window 125 illustrated in FIG. 3A is formed on each of front and rear surfaces of the reaction chamber 120. Also, a substrate of the biochip 130 to be fabricated in the reaction chamber 120 is formed of a transparent material. As such, light that is projected onto the biochip 130 through the front surface of the reaction chamber 120 may be incident on the photodetector 113 through the substrate of the biochip 130 and the rear surface of the reaction chamber 120. Selectively, as described above with reference to FIG. 9, the imaging lens 112 may be omitted and the excitation light absorption filter 115 and the photodetector 113 may be directly attached on the rear surface of the reaction chamber 120 or be disposed proximate to the rear surface of the reaction chamber 120.

As described above with reference to FIG. 9, distortion of an optical image created by the SLM 108' when the biochip 130 is fabricated may be corrected by the distortion correction device 110. However, when the sample is analyzed, a fluorescent image created by the biochip 130 is directly incident on the photodetector 113 without correcting distortion of the fluorescent image. Thus, as illustrated in FIG. 13, a distortion correction device 117 may be added between the reaction chamber 120 and the excitation light absorption filter 115. As such, the distortion correction device 110 disposed between the SLM 108' and the projection optical system 111 may correct image distortion of exposure light, and the distortion correction device 117 disposed between the reaction chamber 120 and the excitation light absorption filter 115 may correct image distortion of fluorescent light.

The present disclosure should not be construed as being limited to the exemplary embodiments set forth herein. Rather, these exemplary embodiments are provided so that this disclosure will be thorough and complete and will fully convey the concept of the exemplary embodiments to those skilled in the art.

Further, although the exemplary embodiments have been shown and described herein, it will be understood by those of ordinary skill in the art that various changes and modifications in form and details may be made therein without departing from the spirit or scope of the claimed invention as defined by the following claims.

For example, although the above exemplary embodiments are described with respect to a refractive optical system that includes a lens or lenses, the same functions and effects may be achieved in a reflective optical system including a concave mirror or a convex mirror. Also, if necessary, the order of optical devices may be changed because various changes in form and details may be made in the above exemplary embodiments by one of ordinary skill in the art.

What is claimed is:

1. An apparatus for fabricating a biochip, the apparatus comprising:
    a reaction chamber which encapsulates the biochip to be sealed from an external environment;
    an exposure system which has a light source and a spatial light modulator, the spatial light modulator receives light from the light source and forms an optical image utilizing the received light, the optical image being received by the biochip;
    a detection system which detects light proceeding from the biochip;
    an optical path changing unit comprising
        a polarizing beam splitter which is disposed between the light source and the spatial light modulator;
        a polarizer which is disposed between the light source and the polarizing beam splitter; and
        a quarter-wavelength plate which is disposed between the polarizing beam splitter and the spatial light modulator; and
    a distortion correction device disposed between the polarizing beam splitter and the reaction chamber, wherein the distortion correction device comprises a deformable mirror having a reflective surface which is deformable in response to at least one of mechanical and electrical manipulation for correcting distortion of the optical image.

2. The apparatus of claim 1, wherein the spatial light modulator is a reflective spatial light modulator.

3. The apparatus of claim 1, wherein the exposure system further comprises:
    a light diffusion device which is disposed between the light source and the polarizer;
    a lens device or a mirror device which is disposed between the quarter-wavelength plate and the spatial light modulator; and
    a projection optical system which is disposed between the distortion correction device and the reaction chamber.

4. The apparatus of claim 1, wherein the detection system is disposed such that the detection system faces one of light exit surfaces of the polarizing beam splitter in order to detect an optical image proceeding from the reaction chamber through the polarizing beam splitter.

5. The apparatus of claim 4, wherein the optical path changing unit further comprises an additional quarter-wavelength plate which is disposed between the polarizing beam splitter and the reaction chamber.

6. The apparatus of claim 1, wherein the detection system is disposed proximate to the reaction chamber along a direction in which light proceeds, in order to detect an optical image which is transmitted through the reaction chamber and the biochip.

7. The apparatus of claim 6, further comprising an additional distortion correction device which is disposed between the reaction chamber and the detection system.

8. The apparatus of claim 1, wherein the spatial light modulator is a transmissive spatial light modulator.

9. The apparatus of claim 8, wherein the exposure system further comprises:
    a light diffusion device and at least one of a lens device and a mirror device which are sequentially disposed between the light source and the spatial light modulator along a direction where light proceeds.

10. The apparatus of claim 9, wherein the detection system is disposed such that the detection system faces one of light exit surfaces of the polarizing beam splitter in order to detect an optical image proceeding from the reaction chamber through the polarizing beam splitter.

11. The apparatus of claim 9, wherein the detection system is disposed proximate to the reaction chamber along a direction in which light proceeds, in order to detect an optical image which is transmitted through the reaction chamber and the biochip.

12. The apparatus of claim 11, further comprising an additional distortion correction device which is disposed between the reaction chamber and the detection system.

13. The apparatus of claim 1, wherein the light source of the exposure system comprises:
- a first light source which emits exposure light which is received by an optical multiplexer; and
- a second light source which emits excitation light which is received by the optical multiplexer, and
- wherein the optical multiplexer selectively transmits or blocks one of the exposure light emitted from the first light source and the excitation light emitted from the second light source.

14. The apparatus of claim 13, further comprising an optical fiber which is disposed between the first light source and the optical multiplexer and further between the second light source and the optical multiplexer.

15. The apparatus of claim 13, wherein the detection system comprises an excitation light absorption filter, at least one of an imaging lens and an imaging mirror, and a photodetector which are sequentially disposed along a direction in which light proceeds.

16. The apparatus of claim 15, wherein the excitation light absorption filter is separated from an optical path when the biochip is fabricated.

17. The apparatus of claim 15, wherein the photodetector is formed of an array comprising a plurality of micro pixels, and comprises one of a photomultiplier tube, a charge-coupled device, and a complementary metal-oxide-semiconductor image sensor.

18. The apparatus of claim 3, wherein the projection optical system is formed by a lens group comprising a plurality of lens elements, wherein at least one lens from the lens group is an aspherical lens.

19. The apparatus of claim 3, further comprising a first optical axis that sequentially includes the light source, the light diffusion device, the polarizer, the polarizing beam splitter, the quarter-wavelength plate, the lens device, and the spatial light modulator; and
- a second optical axis that sequentially includes the polarizing beam splitter, the distortion correction device, the projection optical system, and the reaction chamber.

20. The apparatus of claim 3, wherein the projection optical system comprises a zoom lens.

* * * * *